(12) United States Patent
Knapmeyer et al.

(10) Patent No.: US 9,663,881 B2
(45) Date of Patent: May 30, 2017

(54) NONWOVEN WEBS WITH VISUALLY DISTINCT BOND SITES AND METHOD OF MAKING

(71) Applicant: The Procter & Gamble Company, Cincinnati, OH (US)

(72) Inventors: James Terry Knapmeyer, Cincinnati, OH (US); Dark Saevecke, Wiesbaden (DE); Han Xu, Cincinnati, OH (US); Amy Eichstadt Waun, West Chester, OH (US); J. Michael Bills, Mason, OH (US); Mike P. Purdon, Hebron, KY (US); Olaf Erik Alexander Isele, West Chester, OH (US); Joerg Endres, Langgons (DE)

(73) Assignee: The Procter & Gamble Company, Cincinnat, OH (US)

( * ) Notice: Subject to any disclaimer, the term of this patent is extended or adjusted under 35 U.S.C. 154(b) by 43 days.

(21) Appl. No.: 14/281,928

(22) Filed: May 20, 2014

(65) Prior Publication Data

US 2014/0343526 A1    Nov. 20, 2014

Related U.S. Application Data

(60) Provisional application No. 61/825,303, filed on May 20, 2013.

(51) Int. Cl.
*D04H 1/541*    (2012.01)
*B32B 5/02*    (2006.01)
(Continued)

(52) U.S. Cl.
CPC ....... *D04H 1/541* (2013.01); *A61F 13/15203* (2013.01); *B32B 5/022* (2013.01);
(Continued)

(58) Field of Classification Search
CPC ..... D01F 1/04; D01F 1/06; D01F 8/06; D01F 8/12; D01F 8/00; D01F 8/02; D01F 8/04; D01F 8/08; D01F 8/10; D01F 8/14; D01F 8/16; D01F 8/18; A61F 2013/51026; A61F 2013/51028; A61F 2013/51038; A61F 2013/51377; A61F 2013/51394; A61F 2013/8497
(Continued)

(56) References Cited

U.S. PATENT DOCUMENTS 3,839,002 A    10/1974 Verhoeven et al.
3,860,003 A    1/1975 Buell
(Continued)

FOREIGN PATENT DOCUMENTS

| JP | H 03-33217 A | 2/1991 |
| JP | 2005-229862 A | 9/2005 |
| JP | 4194719 B2 | 12/2008 |

OTHER PUBLICATIONS

PCT International Search Report, mailed Sep. 3, 2014 (11 pages).

*Primary Examiner* — Peter S Vasat
(74) *Attorney, Agent, or Firm* — William E. Gallagher

(57) ABSTRACT

The present invention refers to a nonwoven web with multicomponent fibers having at least a first and a second component which differ from each other in color. The nonwoven web is pattern bonded to obtain bonded areas have a different color versus the unbonded areas.

12 Claims, 1 Drawing Sheet

(51) Int. Cl.

| | |
|---|---|
| B32B 5/26 | (2006.01) |
| A61F 13/15 | (2006.01) |
| B32B 5/06 | (2006.01) |
| B32B 5/08 | (2006.01) |
| B32B 5/12 | (2006.01) |
| B32B 5/22 | (2006.01) |
| B32B 7/02 | (2006.01) |
| B32B 7/04 | (2006.01) |
| B32B 7/12 | (2006.01) |
| B32B 27/08 | (2006.01) |
| B32B 27/12 | (2006.01) |
| B32B 27/20 | (2006.01) |
| D04H 3/147 | (2012.01) |
| D04H 3/16 | (2006.01) |
| D04H 1/4382 | (2012.01) |
| D04H 1/732 | (2012.01) |

(52) U.S. Cl.
CPC .......... *B32B 5/06* (2013.01); *B32B 5/08* (2013.01); *B32B 5/12* (2013.01); *B32B 5/22* (2013.01); *B32B 5/26* (2013.01); *B32B 7/02* (2013.01); *B32B 7/04* (2013.01); *B32B 7/045* (2013.01); *B32B 7/12* (2013.01); *B32B 27/08* (2013.01); *B32B 27/12* (2013.01); *B32B 27/20* (2013.01); *D04H 1/4382* (2013.01); *D04H 1/732* (2013.01); *D04H 3/147* (2013.01); *D04H 3/16* (2013.01); *A61F 2013/15243* (2013.01); *B32B 2250/03* (2013.01); *B32B 2250/20* (2013.01); *B32B 2250/242* (2013.01); *B32B 2262/0253* (2013.01); *B32B 2262/12* (2013.01); *B32B 2305/28* (2013.01); *B32B 2432/00* (2013.01); *B32B 2555/02* (2013.01); *D10B 2509/026* (2013.01); *Y10T 428/2481* (2015.01)

(58) Field of Classification Search
USPC ........................................................ 442/361
See application file for complete search history.

(56) References Cited

U.S. PATENT DOCUMENTS

| | | |
|---|---|---|
| 5,162,074 A | 11/1992 | Hills |
| 5,221,274 A | 6/1993 | Buell et al. |
| 5,266,392 A | 11/1993 | Land et al. |
| 5,280,055 A | 1/1994 | Tomka |
| 5,314,934 A | 5/1994 | Tomka |
| 5,362,777 A | 11/1994 | Tomka |
| 5,370,764 A | 12/1994 | Alikhan |
| 5,554,145 A | 9/1996 | Roe et al. |
| 5,569,234 A | 10/1996 | Buell et al. |
| 5,580,411 A | 12/1996 | Nease et al. |
| 5,844,023 A | 12/1998 | Tomka |
| 5,888,651 A * | 3/1999 | Hoyt .................. D01D 5/253 428/370 |
| 6,004,306 A | 12/1999 | Robles et al. |
| 6,074,590 A * | 6/2000 | Gownder .............. D01D 5/253 264/172.12 |
| 6,090,730 A | 7/2000 | Fujiwara et al. |
| 6,096,809 A | 8/2000 | Loercks et al. |
| 6,214,907 B1 | 4/2001 | Tomka |
| 6,218,321 B1 | 4/2001 | Lorcks et al. |
| 6,231,970 B1 | 5/2001 | Andersen et al. |
| 6,235,815 B1 | 5/2001 | Loercks et al. |
| 6,235,816 B1 | 5/2001 | Loercks et al. |
| 6,242,102 B1 | 6/2001 | Tomka |
| 6,616,435 B2 | 9/2003 | Lee et al. |
| 6,830,810 B2 | 12/2004 | Bond |
| 7,851,391 B2 | 12/2010 | Bond et al. |
| 7,922,943 B2 | 4/2011 | Gerking |
| 7,931,457 B2 | 4/2011 | Johnson et al. |
| 8,173,559 B2 | 5/2012 | Collias et al. |
| 8,231,595 B2 | 7/2012 | Turner et al. |
| 2001/0008683 A1* | 7/2001 | Takai .................... A61F 13/42 428/196 |
| 2005/0164587 A1 | 7/2005 | Melik et al. |
| 2008/0160278 A1 | 7/2008 | Cheng et al. |
| 2011/0264064 A1* | 10/2011 | Arora ............... A61F 13/51496 604/367 |
| 2014/0000003 A1 | 1/2014 | Ashraf et al. |
| 2014/0000784 A1 | 1/2014 | Rane et al. |

* cited by examiner

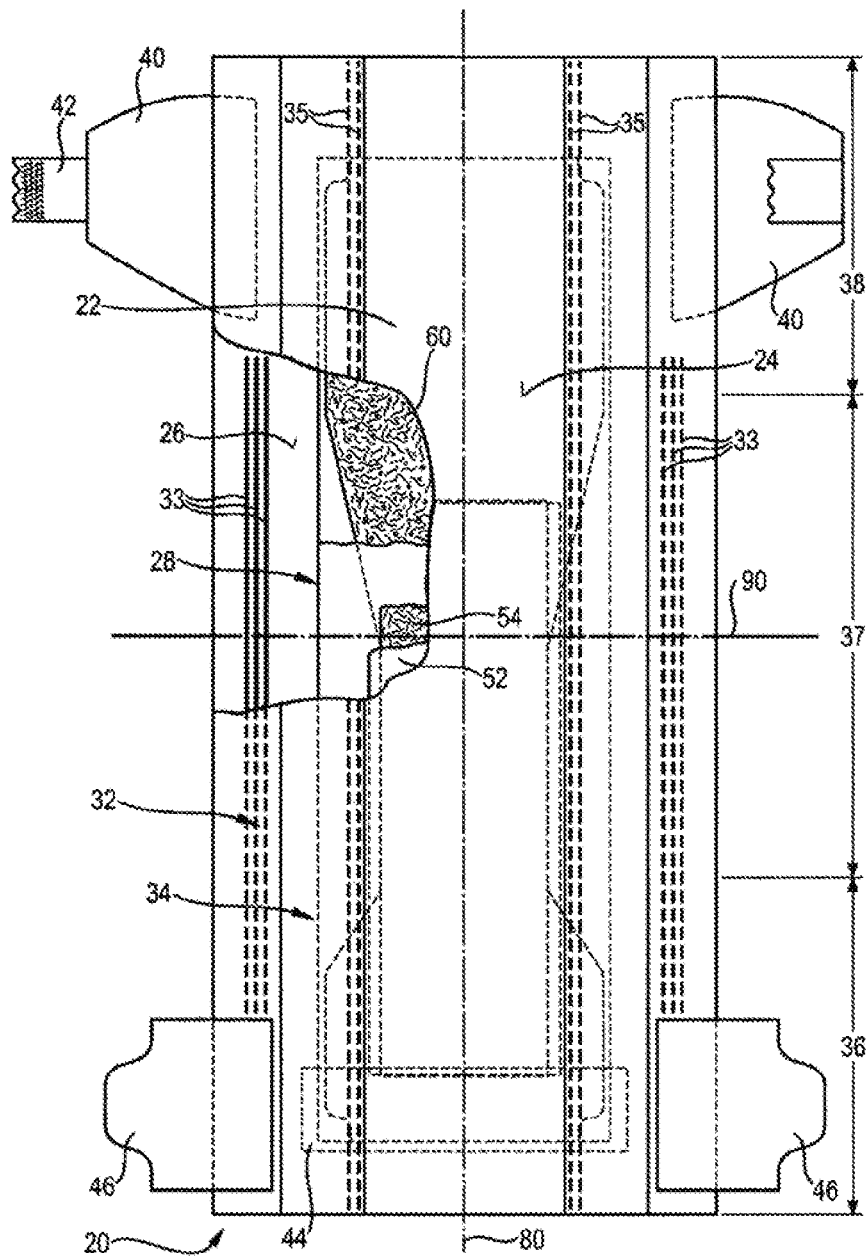

NONWOVEN WEBS WITH VISUALLY DISTINCT BOND SITES AND METHOD OF MAKING

BACKGROUND OF THE INVENTION

Nonwoven webs are widely used in disposable absorbent articles for personal care and hygiene, such as disposable diapers, training pants, adult incontinence undergarments, feminine hygiene products, breast pads, care mats, bibs, wound dressing products, and the like. Also in disposable cleaning articles, such as sweepers or mops, nonwoven webs find intensive application. To make these disposable absorbent articles and disposable cleaning articles more appealing to the consumers, the nonwoven webs used therein are often colored or provided with a printed pattern or graphic. Apart from improving the overall visual appearance of the disposable absorbent articles and disposable cleaning articles, it is often desirable to provide signals to the consumer to highlight certain aspects of features of the disposable absorbent articles, such as softness or the ability to absorb liquid.

Uniformly colored nonwoven webs (e.g., by using homogeneously colored fibers) pose certain restrictions in the ability to accentuate specific aspects, and features because distinct areas within a given nonwoven web cannot be visually set apart from the remaining nonwoven web.

On the other side, printing images on nonwoven webs results in an increase of cost. It requires an additional process step, namely the printing step, in addition to the manufacturing of the nonwoven web. Also, e.g., when used in disposable absorbent articles, the printed images may be rubbed off during use, e.g., when the print is provided on a surface of a nonwoven web which forms a garment-facing surface of the article. Also, if the print is applied on the nonwoven web which forms the inner surface of a disposable absorbent article (such as the topsheet), the inks have to be compatible with surfactants and/or the lotion with which the topsheet may have been treated and must not be washed off when they come into contact with body liquids.

Hence, there is a continued need to provide nonwoven webs having a visual distinct appearance, which can be made in a simple, cost-efficient manner and which do not cause drawbacks, such as rub-off, wash off, or adverse effects on additional treatments of the nonwoven webs, such as application of lotion and/or surfactant.

SUMMARY OF THE INVENTION

The invention refers to a nonwoven web comprising or consisting of multicomponent fibers. The multicomponent fibers have at least a first component and a second component. The second component forms less than 20%, or less than 10% of the outer surface of the multicomponent fibers, or the second component may not be comprised by the outer surface of the multicomponent fibers. The first and the second component differ from each other in color. The nonwoven web is pattern bonded, wherein the bonded areas have a first color and the unbonded areas have a second color which is different from the first color. The difference between the first color of the bonded areas and the second color of the unbonded areas is substantially induced by the difference in color of the components of the multicomponent fibers. The delta E* between the bonded areas and the unbonded areas is at least 0.5, or at least 1.0, or at least 2.5, or at least 3.0, or at least 4.0, or at least 5.0, or at least 10 or at least 15.

The nonwoven web may have a bond pattern which is a consumer noticeable pattern, especially if the nonwoven web is comprised by a disposable absorbent article, such as a disposable diaper.

As the difference between the first color of the bonded areas and the second color of the unbonded areas is substantially induced by the difference in color of the components of the multicomponent fibers (hence, not due to a print provided on a surface of the nonwoven web), possible rub-off of color during use is largely reduced. The nonwoven web may have a color fastness rating of 3.5 and above, or 4 and above. Such color fastness ratings reflect insignificant or no ruff-off of color.

The invention further discloses a method of making a nonwoven web, the method comprising the steps of laying down multicomponent fibers having at least a first component and a second component, the first component having a different color than the second component and wherein the second component forming less than 20% or less than 10% of the outer surface of the multicomponent fibers; or the second component may not be comprised by the outer surface of the multicomponent fibers; and bonding the multicomponent fibers to each other by a bond pattern, wherein the bonded areas have a first color and the unbonded areas a second color, which is different from the first color. The difference between the first color of the bonded areas and the second color of the unbonded areas is substantially induced by the difference in color of the components of the multi component fibers. The delta E* between the bonded areas and the unbonded areas is at least 0.5, or at least 1.0, or at least 2.5, or at least 3.0, or at least 4.0, or at least 5.0, or at least 10 or at least 15.

The bonded areas may be provided by use of heat, pressure, ultrasonic or any combination thereof.

BRIEF DESCRIPTION OF THE DRAWINGS

These and other features, aspects and advantages of the present invention will become better understood with regard to the following description, appended claims, and accompanying drawing where:

FIG. 1 is a plan view of a diaper as an exemplary disposable absorbent article which may comprise the nonwoven web of the present invention.

DETAILED DESCRIPTION OF THE INVENTION

Definitions

"Absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers or diapers for adult incontinence), pants, feminine hygiene products such as sanitary napkins or sanitary pads, breast pads, care mats, bibs, wipes, and the like. As used herein, the term "exudates" includes, but is not limited to, urine, blood, vaginal discharges, breast milk, sweat and fecal matter. Preferred absorbent articles of the present invention are diapers, pants, sanitary napkins, sanitary pads and wipes, such as wet wipes for personal hygiene use.

"Bicomponent" refers to fibers having a cross-section comprising two discrete polymer components, two discrete blends of polymer components, or one discrete polymer component and one discrete blend of polymer components, "Bicomponent fiber" is encompassed within the term "Multicomponent fiber." A Bicomponent fiber may have an overall cross section divided into two subsections of the differing components of any shape or arrangement, including, for example, concentric core-and-sheath subsections, eccentric core-and-sheath subsections, side-by-side subsections, radial subsections, etc. When the bicomponent fibers are used to impart the color different between the bonded and the unbonded areas of the nonwoven web of the present invention, the components of the bicomponent fiber may be made of the same material (i.e. same polymer components or blends thereof) or of different polymer components or blends thereof as long as the first and the second component of the bicomponent fibers differ from each other in color and as long as the first component forms at least 80%, or at least 90%, or 100% of the outer surface of the bicomponent fibers and the second component forms less than 20%, or less than 10% of the outer surface of the bicomponent fibers, or the second component may not be comprised by the outer surface of the bicomponent fibers.

"Bond Area Percentage" on a nonwoven web is a ratio of area occupied, by bond impressions, to the total surface area of the web, expressed as a percentage, and measured according to the Bond Area Percentage method set forth herein.

"Cleaning articles" refers to articles for cleaning household surfaces and clothes, such as sweepers or mops, which comprise dry or wet-type disposable cloths typically used for mopping or sweeping lint. Cleaning articles also comprises laundry bags, dryer bags and cleaning sheets.

"Color", as used herein, includes any color in the CIELAB color space including primary color, secondary color, tertiary color, the combination thereof as well as black and white. As used herein "white" is defined as having $L^*>90$, $-2<a^*<2$, and $-2<b^*<2$.

CIE $L^*a^*b^*$ ("CIELAB") is the most commonly used color space specified by the International Commission on Illumination (French Commission internationale de l'eclairage, hence its CIE initialism). It describes all the colors visible to the human eye and was created to serve as a device independent model to be used as a reference.

The three coordinates of CIELAB represent the lightness of the color ($L^*=0$ yields black and $L^*=100$ indicates diffuse white; specular white may be higher), its position between red/magenta and green ($a^*$, negative values indicate green while positive values indicate magenta) and its position between yellow and blue ($b^*$, negative values indicate blue and positive values indicate yellow). The asterisk (*) after L, a and b are part of the full name, since they represent $L^*$, $a^*$ and $b^*$, to distinguish them from Hunter's L, a, and b.

"Cross direction", with respect to a web material, refers to the direction along the web material substantially perpendicular to the direction of forward travel of the web material through the manufacturing line in which the web material is manufactured.

"Disposable" is used in its ordinary sense to mean an article that is disposed or discarded after a limited number of usage events over varying lengths of time, for example, less than 20 events, less than 10 events, less than 5 events, or less than 2 events. If the disposable absorbent article is a diaper, a pant, sanitary napkin, sanitary pad or wet wipe for personal hygiene use, the disposable absorbent article is most often disposed after single use.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pant" which is defined below.

"Machine direction", with respect to a web material, refers to the direction along the web material substantially parallel to the direction of forward travel of the web material through the manufacturing line in which the web material is manufactured.

"Monocomponent" refers to fiber formed of a single polymer component or single blend of polymer components, as distinguished from Bicomponent or Multicomponent fiber.

"Multicomponent" refers to fiber having a cross-section comprising two or more discrete polymer components, two or more discrete blends of polymer components, or at least one discrete polymer component and at least one discrete blend of polymer components.

"Multicomponent fiber" includes, but is not limited to, "bicomponent fiber."

"Multilayered nonwoven web" is a nonwoven web which is made of several fiber layers, wherein the layers have been laid down, on top of one another, in one continuous manufacturing process, wherein the fibers of the multilayered nonwoven web are consolidated and bonded together to form a self-sustaining web only alter the several layers of fibers have been laid down. Hence, the fibers within the different layers have not been substantially bonded together prior to assembling into a multilayered nonwoven web, but instead the fibers of all layers are pattern-bonded together after assembly into a multilayered nonwoven web. However, the individual layers may have undergone a compaction step, typically by passing the layer through the nip between two rollers, or by a roller pressing onto the fibrous layers on top of the moving lay down belt. Such compaction step does not result in the formation of discernible fused bond sites. Laminates made of preformed, self-sustaining webs are consequently not encompassed by the term "multilayered nonwoven web" as used herein.

A "nonwoven web" is a manufactured web of directionally or randomly oriented fibers, consolidated and bonded together by one or more patterns of bonds and bond impressions created through localized compression and/or application of heat or ultrasonic energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunlaid, solvent spinning, electrospinning, and carding. As used herein, "spunlaid" refers to fibers made by spunbond technology without having undergone further processing, such as bonding. The basis weight of nonwoven fabrics is usually expressed in grams per square meter (gsm). For the present invention, a nonwoven web may be consolidated and bonded by hydroentanglement and/or needle punching, in addition to being consolidated and bonded by bonds obtained by heat and/or compression (including ultrasonic bonding), e.g. in order to impart improved loft to the nonwoven web.

"Pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

Disposable Absorbent Articles

A typical disposable absorbent article comprising the nonwoven web of the present invention is represented in FIG. 1 in the form of a diaper 20.

In more details, FIG. 1 is a plan view of an exemplary diaper 20, in a flat-out state, with portions of the structure being cut-away to more clearly show the construction of the diaper 20. This diaper 20 is shown for illustration purpose only as the nonwoven web of the present invention may be comprised in a wide variety of diapers or other absorbent articles.

As shown in FIG. 1, the absorbent article, here a diaper, can comprise a liquid pervious topsheet 24, a liquid impervious backsheet 26, an absorbent core 28 which is preferably positioned between at least a portion of the topsheet 24 and the backsheet 26. The absorbent core 28 can absorb and contain liquid received by the absorbent article and may comprise superabsorbent polymer 60. The diaper 20 may also include optionally an acquisition system with an upper and lower acquisition layer (52 and 54).

The diaper may also comprise elasticized leg cuffs 32 and barrier leg cuffs 34, and a fastening system, such as an adhesive fastening system or a hook and loop fastening member, which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, which are not represented, such as a back elastic waist feature and a front elastic waist feature, side panels or a lotion application.

The diaper 20 as shown in FIG. 1 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

The chassis 22 of the diaper 20 comprises the main body of the diaper 20. The chassis 22 comprises the absorbent core 28 and preferably an outer covering including the topsheet 24 and/or the backsheet 26. The majority of diapers are unitary, which means that the diapers are formed of separate parts united together to form a coordinated entity so that they do not require separate manipulative parts like a separate holder and/or liner.

The chassis 22 comprises the main structure of the diaper with optional other features such as back ears 40, front ears 46 and/or barrier cults 34 attached to form the composite diaper structure. The topsheet 24, the backsheet 26, and the absorbent core 28 may be assembled in a variety of well known configurations, in particular by gluing or heat embossing. Exemplary diaper configurations are described generally in U.S. Pat. No. 3,860,003, U.S. Pat. No. 5,221,274, U.S. Pat. No. 5,554,145, U.S. Pat. No. 5,569,234, U.S. Pat. No. 5,580,411; and U.S. Pat. No. 6,004,306.

The diaper 20 may comprise leg cuffs 32 which provide improved containment of liquids and other body exudates. Leg cuffs 32 may also be referred to as leg bands, side flaps, barrier cuffs, or elastic cuffs. Usually each leg cuffs will comprise one or more elastic string 33, represented in exaggerated form on FIG. 1 comprised in the chassis of the diaper for example between the topsheet and backsheet in the area of the leg openings to provide an effective seal while the diaper is in use. It is also usual for the leg cuffs to comprise "stand-up" elasticized flaps (barrier leg cuffs 34) which improve the containment of the leg regions.

Of course, it will be recognized that any disposable absorbent article design may comprise one or more nonwoven webs of the present invention. The disclosure above is merely for illustrative purposes.

Nonwoven Webs Comprising Multicomponent Fibers

The present invention is directed, towards a nonwoven web comprising or consisting of multicomponent fibers, such as bicomponent fibers.

A multicomponent fiber has an overall cross section divided, into subsections of the differing components of any shape, for example round, trilobal or ribbon-shaped, and any arrangement, including, for example, coaxial subsections, concentric core-and-sheath subsections, eccentric core-and-sheath subsections, side-by-side subsections, islands-in the sea subsection, segmented pie subsections, etc. To make a multicomponent fiber, at least two polymer streams are extruded to form a unitary fiber. A method to produce these multicomponent fibers, or one or multiple layers comprising multicomponent fibers, is described in U.S. Pat. No. 5,162,074.

The cross-sectional components of multicomponent fibers are substantially constantly positioned in distanced "zones" across the cross section of the fiber and extend substantially continuously along the length of the multicomponent fibers. In core-and-sheath fibers, the fiber's geometric configuration of components is such that at least one cross-sectional component is substantially completely surrounded by another cross sectional component. In core-sheath multicomponent fibers having more than two components, a first and a second component may form an outer and an inner sheath component and a third component may form the core component. The fibers may also be hollow, such that a first component may form the outer sheath component and a second component may form an inner sheath component (with the core being hollow).

In multicomponent fibers used to impart the color different between the bonded, and the unbonded areas of the nonwoven web of the present invention, the components of the multicomponent fiber may be made of the same material (i.e. same polymer components or blends thereof) or of different polymer components or blends thereof as long as a first and the second component of the multicomponent fibers differ from each other in color (e.g. by use of different pigmentation) and as long as the second component forms less than 20%, or less than 10%, of the outer surface of the multicomponent fibers or the second component may not be comprised by the outer surface of the multicomponent fibers. The first component may form at least 50%, or at least 80% or the entire outer surface of the multicomponent fibers.

The multicomponent fibers have at least a first and a second component, which differ from each other in color. As used herein, "difference in color" or "to differ in color" includes different colors (such as blue and green, or green and white) as well as different shades of the same color (such as lighter blue and darker blue). Also, as used herein, white, black, and shades of grey are considered as colors. The difference in color between the first and the second component needs to be large enough to obtain a delta E* of at least 0.5 between bonded and unbonded areas of the nonwoven web after the nonwoven web has been pattern bonded (as explained in more detail below). The difference in color may be obtained by using different pigmentation for the first and second component of the multicomponent fibers.

The nonwoven web is pattern bonded. Typically, the bond pattern is imparted by use of heat and/or pressure, and/or by ultrasonic bonding. Due to the use of heat, pressure and/or ultrasonic energy, the multicomponent fibers in the bond areas are pressed tightly together, which results in plastic deformation of the fibers. Especially if bonding is achieved by heat, or by heat and compression, the fibers in the bonded areas are molten, completely or partially, such that in the bonded areas the individual fibers are fused together (coalescence) to form a film-like structure. In the bonded areas, the deformed/fused fibers comprise the material of the first and second fiber component (and of the optionally further components).

Due to this bonding, the material of the second component of the multicomponent fibers becomes more discernible in the bonded areas. In the pattern bonded nonwoven web, the visual appearance of the unbonded areas is mainly determined by the visual appearance of the components) forming the outer surface of the fibers. In a core-and-sheath fiber, the first component forming the outer surface of the fiber will hence mainly determine the visual appearance of the unbonded areas. In multicomponent fibers where the second component is surrounded by the first and further components, the visual appearance of the unbonded areas will be mainly determined by the components which form the outer surface, for example in a multicomponent fiber wherein the second component forms the core of the fiber while the first and third components together form the outer surface of the fiber. The visual appearance of the bonded areas is determined by the first and the second component of the multi-component fibers, as well as by the color of the optional further components. In the unbonded areas, the component(s) which form the outer surface of the multi-component fibers refracts the light which "masks" the second component. This masking effect is generally increased with increased level of pigment(s).

The masking effect is also affected by die share die second component has in the overall multicomponent fiber (i.e. the percentage of the second component in the overall cross-sectional area of the fiber). If the second component forms a relatively small portion of the multicomponent fiber, the masking effect is increased versus multicomponent fibers wherein the second component forms a relatively large portion of the multicomponent fibers.

On the other hand, if the second component forms a relatively small percentage of the overall cross-sectional area of the fiber, the color difference between bonded and unbonded areas may be too small, such that a delta E* of at least 0.5 between bonded and unbonded areas cannot be obtained. If the color difference between the second component and the first (and optional further components) is however, substantial and distinct enough, a delta E* of at least 0.5 between bonded and unbonded areas may also be obtained with multicomponent fibers wherein the second component forms only a relatively small percentage of the overall cross-sectional area of the fiber.

For the present invention, the second component may form less than 60%, or less than 50% or less than 40% of the cross-sectional area of the multicomponent fiber.

Generally, for good masking properties, the first component and/or the optional further component(s) forming the outer surface of the fiber may have an opacity greater than 30%, or greater than 35%, or greater than 40%, or greater than 45%, or greater than 50% as measured according to the test method set out herein below. Good opacity may be obtained by white pigmentation, such as $TiO_2$, or by other methods known in the art for increasing fiber opacity.

In the bonded areas, the fibers are deformed and pressed or fused together such that the bonded areas do not have individual fibers which scatter and diffract light, and the fused fiber mass creates a distinct visual appearance. It may also happen that a certain level of inter-component mixing may occur in the bonded areas due to compression/fusion of fibers, which improves the distinct color appearance in the bonded areas as the second component is colored differently from the first component.

The components of the multicomponent fibers should be selected such that the difference in color between the first, second and optional further components results in the bonded areas having a first color and the unbonded areas having a second color which is different from the first color. The delta E* between the bonded areas and the unbonded areas is at least 0.5 as determined by the Test Method disclosed herein below. The delta E* between the bonded areas and the unbonded areas may be at least 1.0 or at least 2.0, or at least 2.5, or at least 3.0, or at least 4.0, or at least 5.0, or at least 10 or at least 15. It has been found that a delta E* of 0.5 is already sufficient to obtain bond areas which are visually distinct from the unbonded areas, such that the visual difference is noticeable to the naked eye. However, as delta E* increases, the bonded areas become more distinguishable and more pronounced versus the unbonded areas.

Further color distinctions can be found using delta C* and delta H*. It has been found that a sufficient and significant color distinction can be achieved by providing a nonwoven web which may have delta C* of at least 1, or at least 3 or at least 5 between the bonded areas and the unbonded areas. Also, sufficient and significant color distinction can be achieved by providing a nonwoven web which may have delta H* of at least 1, or at least 1.2, or at least 1.5, or at least 2 between the bonded areas and the unbonded areas.

Notably, in the nonwoven webs of the present invention, the areas having different color are congruent with the bonded areas, as the different color is obtained simultaneously with introducing the bond pattern. Hence, by simply imparting a print on a surface of a (uniformly colored) nonwoven web to "mimic" the effect of the present invention, the same visual effect can only be achieved if the print is exactly registered with the bonded areas, thus requiring a very exact and demanding manufacturing process. However, even if using such expensive and complex manufacturing process, the resulting nonwoven web would still have the drawbacks mentioned above, e.g. increases risk of rub-off or wash-off of the print during use. For the present invention, the delta E* between the bonded and the unbonded areas of at least 0.5, or at least 1.0, or at least 2.5, or at least 3.0, or at least 4.0, or at least 5.0, or at least 10 or at least 15 is obtained by the difference in color between the different components of the multicomponent fibers of the nonwoven web and is not obtained by providing a print (which corresponds with the bond pattern) on a surface of the nonwoven web.

Bonded areas are typically areas of reduced thickness in a nonwoven web (as the fibers have been compressed and/or fused together). It has been found that the congruence between difference in color and difference in thickness of the nonwoven web results in a nonwoven web which is perceived as having enhanced 3-dimensional appearance and, e.g. if used as topsheet for absorbent articles, as having good fluid handling properties (suggesting fast liquid uptake).

The multicomponent fibers of the nonwoven web comprise at least a first and a second, component. The multicomponent fibers may consist only of the first and second component. However, the multicomponent fibers may comprise further components. The components of the multicomponent fibers may be arranged in any pattern (with regard, to the cross-section of the fiber) as long as the second component forms less than 20% or less than 10% of the outer surface of the multicomponent fibers, or if the outer surface does not comprise the second component at all.

The nonwoven web of the present invention may consist solely of multicomponent fibers having at least a first component and a second, component, with the second component forming less than 20% of the outer surface of the multicomponent fibers, and wherein the first and the second component, differ from each other in color. Alternatively, the nonwoven web of the present invention may comprise other fibers in addition to this kind of multicomponent fibers. For example, the nonwoven web may comprise monocomponent fibers or multicomponent fibers others than those described in the beginning of this paragraph.

The nonwoven web of the present invention may be a monolayer nonwoven web. If the nonwoven web of the present invention has only one layer, the nonwoven web may comprise at least 70% by weight, or at least 80% by weight, or at least 90% by weight of multicomponent fibers having at least a first component and a second, component, with the second component forming less than 20% of the outer surface of the multicomponent fibers, and wherein the first and the second component differ from each other in color.

The nonwoven web of the present invention may also be a multilayer nonwoven web. If the nonwoven web is a multilayer nonwoven web, at least one of the layers will comprise at least 70% by weight, or at least 80% by weight, or at least 90% by weight, or 100% by weight of multicomponent fibers having at least a first component and a second component, with the second component, forming less than 20% of the outer surface of the multicomponent fibers, and wherein the first and the second component differ from each other in color. The nonwoven web may also comprise more than one layer comprising or consisting of these multicomponent fibers, and in one embodiment, all layers of a multilayer nonwoven may comprise or consist of these multicomponent fibers. Further layers of a multilayer nonwoven web may also consist of other fibers, such as monocomponent fibers and/or other kinds of multicomponent fibers. If the nonwoven web of the present invention is a multilayer nonwoven web, at least one of the layers forming the outer surface of the nonwoven web may comprise or consist of multicomponent fibers having at least a first component and a second component, with the second component forming less than 20% of the outer surface of the multicomponent fibers, and wherein the first and the second, component differ from each other in color.

Suitable nonwoven webs useful in the present invention comprise spunlaid layers, meltblown layers and layers of nanofibers. Generally, the diameter of spunlaid fibers is larger compared to the diameter of meltblown fibers, which in turn have a somewhat larger diameter than nanofibers. Spunlaid fibers typically have a diameter of 8 µm to 40 µm; meltblown fibers have a diameter of 0.5 µm to ≤8 µm, while nanofibers generally have a diameter of 0.01 µm to 1.5 µm. Nanofibers can be made by different processes, including advanced meltblown as disclosed in U.S. Pat. No. 7,922,943B2, melt film fibrillation as disclosed in U.S. Pat. No. 7,931,457B2 or electrospinning as disclosed in U.S. Pat. No. 6,616,435B2. The spunlaid fibers may also have non-circular cross-sections, in winch case the major and minor axes of the cross-sectional shape have lengths in the range from 8 µm to 40 µm.

The nonwoven web may also be made of carded fibers (so-called staple-fibers) or the nonwoven web may be a multilayer nonwoven web comprising one or more layers of carded fibers and one or more layers of spunlaid, meltblown and/or nano fibers. Examples include, but are not limbed to SMS multilayer nonwoven webs, comprising a spunlaid, a melt-blown and a further layer. Another suitable multilayer nonwoven web of the present invention comprises a SMMS-structure (two outer spunlaid layers and two inner melt-blown layers) or a SMMMS-structure (two outer spunlaid layers with three inner meltblown layers). Other suitable multilayered nonwoven webs are SNS materials, comprising a spunlaid, a nanofiber and a further spunlaid layer, or SMNS materials, comprising a spunlaid, a meltblown, a nanofiber and a further spunlaid layer.

Nonwoven webs having spunlaid fibers forming the outer surfaces of the nonwoven web tend to have better resistance to fuzz, i.e. the fibers exposed to the surface of the nonwoven web are not as easily abraded and twitched out of the nonwoven web as fine fibers with smaller diameters (such as meltblown fibers or nanofibers). This may be especially beneficial when nonwoven web forms at least a part of the garment-facing surface of a disposable absorbent article, such as a diaper, where the garment-facing surface is rubbed against clothes or other items (such as carpets) when the article is worn.

On the other hand, nonwoven webs, wherein the outer surface is formed of a meltblown fibers or nanofibers may be able to provide a more uniform appearance on the outer surface at a given basis weight of the fiber layer as the fibers have a considerably smaller diameter.

In the nonwoven web of the present invention, at least the multicomponent fibers having at least a first component and a second component, with the second component forming less than 20% of the outer surface of the multicomponent fibers, and wherein the first and the second component differ from each other in color, may be formed of thermoplastic material, such as, for example, polyolefin, polyesters, polyamide or specifically polypropylene (PP), polyethylene (PE), poly-lactic acid (PLA), polyethylene terephthalate (PET), Nylon 6-6 as well as combinations thereof (such as blends and copolymers).

All of the fibers of the nonwoven web of the present invention may be formed from thermoplastic material, such as polyolefin, polyesters, polyamide or specifically polypropylene (PP), polyethylene (PE), poly-lactic acid (PLA), polyethylene terephthalate (PET), Nylon 6-6 as well as combinations thereof (such as blends and copolymers). However, if the nonwoven web of the present invention is a multilayer nonwoven web, one or more of the layers may be made of non-thermoplastic fibers, such as natural fibers, provided that a sufficient number of thermoplastic fibers are comprised in the bonded areas (hence, such nonwoven webs should comprise one or more layers of thermoplastic fibers). In such embodiments, the layer(s) comprising or consisting of the multicomponent fibers having at least a first component and a second component, with the first component forming at least 80% of the outer surface of the multicomponent fibers, and wherein the first and the second component differ from each other in color, may be formed of thermoplastic material, such as polyolefin, polyesters, polyamide or specifically polypropylene (PP), polyethylene (PE), poly-lactic acid (PLA), polyethylene terephthalate (PET), Nylon 6-6 as well as combinations thereof (such as blends and copolymers).

Generally, resins including PP may be particularly useful because of polypropylene's relatively low cost, low density and surface friction properties of fibers formed from it (i.e., they have a relatively smooth, slippery tactile feel), as well as their good mechanical properties. Resins including PE may also be desirable because of polyethylene's relative softness/pliability and even more smooth/slippery surface friction properties. Relative to each other, PP currently has a lower cost and fibers formed from it have a greater tensile strength, while PE currently has a greater cost and fibers formed from it have a lower tensile strength but greater pliability and a more smooth/slippery feel. Multicomponent fibers from PP and PE are desirable for as they combine the good softness properties of PE and the good mechanical properties of PP.

Accordingly, it may be desirable to form web fibers from a blend of PP and PE resins, finding a balance of the best proportions of the polymers to balance their advantages and disadvantages. In some examples, the fibers may be formed of PP/PE blends such as described in U.S. Pat. No. 5,266,392.

The thermoplastic polymer suitable for the fibers comprised by the nonwoven webs of the present invention may also be thermoplastic starch. As used herein, "thermoplastic starch" or "TPS" means a native starch or a starch derivative that has been rendered destructured and thermoplastic by treatment with one or more plasticizers, with at least one starch plasticizer still remaining. Thermoplastic starch compositions are well known and disclosed in several patents, for example: U.S. Pat. Nos. 5,280,055; 5,314,934; 5,362,777; 5,844,023; 6,214,907; 6,242,102; 6,096,809; 6,218,321; 6,235,815; 6,235,816; and 6,231,970. TPS may be used for the multicomponent fibers of the present invention having at least a first component and a second component, with the second component forming less than 20% of the outer surface of the multicomponent fibers, and wherein the first and the second component differ from each other in color. TPS may form the first component, the second component, or both. TPS may also form the optional additional further components of the multicomponent fibers. In one embodiment, the first component of the multicomponent fibers is made of a polyolefin and the second component is made of TPS.

The nonwoven web may have any basis weight. However, relatively higher basis weight, while having relatively greater apparent caliper and loft, also has relatively greater cost. Suitable basis weight for nonwovens of the present invention have been found to be 200 gsm or less, or from 4 gsm to 80 gsm, or from 5 gsm to 50 gsm, or from 8 gsm to 30 gsm. For the present invention it may generally be desirable to have nonwoven webs with relatively homogeneous distribution of fibers, i.e. webs wherein the fibers have been laid down homogeneously, especially for nonwoven webs with relatively low basis weight.

The first component of the multicomponent fibers may comprise a white pigment. Thereby, in the unbonded regions the first component can provide good opacity to conceal the second component and the optional further components. One example of a suitable white pigment is titanium dioxide ($TiO_2$). $TiO_2$ provides brightness and relatively high refractive index. It is believed that addition of $TiO_2$ to the polymer(s) from which the first component may be formed, in an amount up to 5.0% by weight of the first component, may be effective to achieve the desired results. However, because $TiO_2$ is a relatively hard, abrasive material, inclusion of $TiO_2$, in amounts greater than 5.0% by weight may have deleterious effects, including wear and/or clogging of spinnerets; interruption and weakening of the structure of the fibers and/or calender bonds there between; undesirably increasing the surface friction properties of the fibers (resulting in a less smooth tactile feel); and unacceptably rapid wear of downstream processing equipment components. While 5.0% by weight $TiO_2$ may be an upper limit, it may be more desirable to have a first component including no more than 4.0% or no more than 3.0% or no more than 2.0% $TiO_2$ by weight of the first component.

The first component and the second component of the multicomponent fibers may differ from each other in pigmentation. If the multicomponent fibers comprise one or more additional component(s), the one or more additional component(s) may differ in pigmentation from the first and second component. Alternatively, the one or more additional components) may have the same pigmentation as the first or second, component. One or more additional component(s) forming a substantial part of the outer fiber surface (such as at least 30%) may have the same or similar pigmentation as the first component. One or more additional component(s) forming no substantial part of the outer fiber surface (such as less than 30%, or less than 20%, or less than 10%) may have the same or similar pigmentation as the second component.

As used herein, to "differ in pigmentation" or "difference in pigmentation" means
a) the first component comprises a pigment which is different from the pigment of the second component; or
b) the first component comprises a different combination of pigments; or
c) the first component comprises different amounts of the same pigment(s) versus the second component—for example, the first component may have at least 5 times, or at least 10 times the amount of the same pigment(s) of the second component; or
d) combinations of any of options a) to c).

A pigment is a material, which can be organic or inorganic. A pigment changes the color of reflected or transmitted light as the result of wavelength-selective absorption. This physical process differs from fluorescence, phosphorescence, and other forms of luminescence, in which a material emits light. A pigment is a generally insoluble powder, which differs from a dye, which either is itself a liquid or is soluble in a solvent (resulting in a solution). Dyes are often used to provide a print on the surface of a nonwoven web, such as graphics, pattern or images. Hence, these dyes do not form a part of the fibers (or of the component of multicomponent fibers) of the nonwoven web but are rather applied on the web surface. Contrary thereto, in the present invention the pigments are comprised within the multicomponent fibers—at least in one or more of the components—of the nonwoven web, which eliminates the risk of rub-off or wash-off of the colour(s) imparted to the nonwoven web by the pigment.

Generally, the color of the bonded areas shall be permanent. No use of thermochromic pigments and/or pressure sensitive pigments in the fibers of the nonwoven web of the present invention shall not comprise any thermochromic pigments and/or pressure sensitive. This is also beneficial, as thermochromic pigments and/or pressure sensitive pigments are relatively expensive (vs. many other pigments).

The pigment will typically be mixed with the thermoplastic material, of which one or more of the components of the multicomponent fibers are made. Often, the thermoplastic material is colored in a so-called masterbatch, wherein a large quantity of thermoplastic material is molten and colored with one or more pigments. The homogeneously colored thermoplastic material is then solidified and typically formed into pellets, which can be used for the manufacture the components of the multicomponent fibers to be formed into the nonwoven web. Colored masterbatches useful for the present invention are Lufilen and Luprofil supplied by BASF; Remafin for polyolefin fibers, Renol-AT for polyester fibers, Renol-AN for polyamide fibers and CESA for renewable polymers supplied by Clariant. Hence, the pigment will be suspended in the molten thermoplastic material prior to the thermoplastic material being forced through the spinnerets to form and lay down the fibers which form the nonwoven web.

Fillers are particles which are often added to materials, such as the fibers of nonwoven webs, to lower the consumption of more expensive materials, such as the thermoplastic material of the fibers (e.g. polyethylene, polypropylene). However, the fillers may also be more expensive than the thermoplastic materials of the fibers and may be used to impart desired properties to the fibers and the resulting nonwoven webs or to improve the process ability of thermoplastic material (such as reduction of melt viscosity). For the present invention, the fillers may be selected to impart or at least contribute to the difference in color between the first and second component of the multicomponent fibers, and thus to the difference in color between the bonded, areas and the unbonded areas of the nonwoven web. Filler particles can be organic or inorganic. A typical example of filler is titanium dioxide, which can impart a white color. Another example is calcium carbonate ($CaCO_3$), which can also provide for a higher opacity. For the present invention, fillers are considered as pigments, as long as they are able to impart a color to components of the multicomponent fibers (such as the white color imparted by titanium dioxide).

Generally, it may be desirable that the first component has a lighter color than the second component of the multicomponent fibers (i.e. the color has a higher $L^*$ value), such that the bonded areas take a more intense and/or darker color compared to the unbonded areas.

The second component, of the multicomponent fibers may be of non-white color.

The second component may thus comprise a non-white pigment, such as a blue pigment, a yellow pigment or a green pigment.

The multicomponent fibers may comprise additional components, such that the multicomponent fibers may have three, four, five, six, or more components. The additional component(s) may have the same color or a different color than the first component and/or the additional components may have the same color (if the color is different from the first component) and/or the additional components may have a different color than the second component. Thus, the additional component(s) may differ in pigmentation from the first and/or second component. Alternatively, the additional component(s) may have the same pigmentation as the first or second component. In a still further alternative, the additional components) may be free from pigmentation.

If the nonwoven web comprises more than one further component in addition to the first and second component, these additional components may all have the same or similar color (e.g. same or similar pigmentation). Alternatively, the additional components may differ from each other with regard to their color (e.g. by different pigmentation). Also, one or more additional component(s) may comprise one or more pigments) while one or more other additional component(s) may be free from pigmentation.

Given the many possible variations when combining different first and second components and optional further component(s), it is apparent that the present invention allows for numerous possible embodiments with all kinds of color combinations of the bonded areas and the unbonded areas so that a very large variety of different nonwoven webs can be obtained.

The nonwoven web of the present invention is pattern bonded. As used herein, the term "pattern bonded" comprises a plurality of individual bonded areas (which may be arranged as a repeating pattern) winch are surrounded by continuous unbonded areas, as well as a continuous bonded area which surrounds a plurality of individual unbonded areas. Also, the term "pattern bonded" comprises bonded areas and unbonded areas which are alternating with each other, e.g. as stripes or waves extending in machine direction or cross-direction. The overall bonded area, i.e. the sum of all bonded areas taken together, should be from 5% to 80% of the overall area of the nonwoven web, or from 5% to 50%, or from 10% to 40% of the overall area of the nonwoven web. The overall bonded area may be determined by the Test Method on Bond Area Percentage below. However, if the bonded areas are introduced by calender bonding, the percentage of the raised areas on the pattern roll with regard, to the overall surface area of the patterned calender roll can be taken as the bonded area.

If the nonwoven web has a plurality of individual bonded areas, the size of the individual bonded areas comprised by the bond pattern of the nonwoven web may be at least 0.3 $mm^2$, or at least 0.4 $mm^2$ or at least 0.5 $mm^2$ or at least 0.7 $mm^2$; they may also be no more than 10 $mm^2$ or no more than 5 $mm^2$. If individual bonded areas are not ail similar in size, the size of all individual bonded areas may be in the range of from 0.3 $mm^2$ to 10 $mm^2$ or from 0.4 $mm^2$ to 8 $mm^2$ or from 0.5 $mm^2$ to 8 $mm^2$. Generally, for nonwoven webs wherein delta $E^*$ between the bonded and unbonded areas is relatively large (such as greater than 5, or greater than 10), smaller individual bonded areas (such as 0.3 $mm^2$ to 0.6 $mm^2$) may be easily visible to the naked eye, whereas for a smaller delta $E^*$ (such as smaller than 5) it may be desirable to have slightly larger individual bonded areas (such as larger than 0.6 $mm^2$). Also, for nonwoven webs having a relatively high basis weight (such as greater than 12 gsm, or greater than 15 gsm), smaller individual bonded areas (such as 0.3 $mm^2$ to 0.5 $mm^2$) may be easily visible to the naked eye, whereas for a lower basis weights (such as smaller than 15 gsm, or smaller than 12 gsm) it may be desirable to have slightly larger individual bonded areas (such as larger than 0.6 $mm^2$). Bond pattern that can be easily perceived by the consumer to communicate design attributes are preferred. A "consumer noticeable pattern" as used herein is a pattern with an area of at least 0.6 $mm^2$ or at least 0.9 $mm^2$, preferably more than 2 $mm^2$; with bonding area percentage which may be at least 5% or at least 10%. The bonding area percentage may be less than 50%, or less than 25%, or less than 20%; or even less than 15%.

The nonwoven web of the present invention can be used in an absorbent article, such as the disposable diaper described above. For example, the nonwoven web may form a portion of or the whole of the topsheet, the backsheet, the back ears, the front ears, the fastening system (such as at least a portion of the landing zone or the fastening tapes), the elasticized leg cuffs and/or the barrier leg cuffs.

The nonwoven web can be made by the following method:

Multicomponent fibers are laid down. The multicomponent fibers have at least a first component and a second component, which differ from each other in color. The second component forms less than 20% of the outer surface of the multicomponent fibers. The multicomponent fibers may be laid down together with other fibers, such as monocomponent fibers or multicomponent fibers being different from the multicomponent fibers having at least a first component and a second component, being different from each other in color and wherein the second component forms less than 20% of the outer surface of the multicomponent fibers. The fibers are typically laid down on a support member, such as a belt or a drum. If the nonwoven web comprises multiple layers, the fibers of the different layers are laid down subsequently, one on top of the other. One, more than one or all of the layers may then comprise or consist of multicomponent fibers having at least a first component and a second component, differing from each other in color, with the second component forming less than 20% of the outer surface of the multicomponent fibers.

The first and the second component of the multicomponent fibers differ from each other in color, e.g. by differing from each other in pigmentation.

The fibers may be made of molten thermoplastic material which is processed into fibers by a suitable method as is well known in the art, such as spunlaid, meltblown or carded processes.

In spunlaid processes polymer granules are melted and molten polymer is extruded through spinnerets. The continuous fibers are drawn, cooled and deposited on to a conveyor to form a uniform web. Some remaining elevated temperature near the melt temperatures may cause fibers to adhere to one another, but this cannot be regarded as the principal method of bonding. This principal method of bonding is thermal point bonding. The spunlaid process (also known as spunbonded) has the advantage of giving fibers and resultant nonwoven webs with relatively good strength.

In meltblown web formation, low viscosity polymers are extruded into a high velocity airstream on leaving the spinneret. The extruded fibers are rapidly drawn to fine diameters, solidify and may break into shorter fibers during this drawing and laydown process before collecting the fibers in the form of a fibrous web. There may be enough fiber bonding and entangling to form a cohesive web layer that has some integrity without subsequent additional bonding step.

Carding is a mechanical process which generally starts with the opening of bales of fibers which may be blended and conveyed to the next stage by air transport. The fibers are then combed into a web by a carding machine, which is a rotating drum or series of drums covered, in wires or teeth. The precise configuration of wires and cards will depend on the fiber type, fabric weight and fiber orientation required.

The web can be parallel-laid, where most of the fibers are laid in the direction of the web travel, or they can be random-laid.

After being laid down, the fibers are bonded to each other by a bond pattern. The resulting bonded areas of the mono- or multilayer nonwoven web have a first color and the unbonded areas have a second color, which is different from the first color. The difference between the first color of the bonded areas and the second, color of the unbonded areas is substantially induced by the difference in color of the components of the multicomponent fibers. The delta E* between the bonded areas and the unbonded areas is at least 0.5, or at least 1.0, or at least 2.5, or at least 3.0, or at least 4.0, or at least 5.0, or at least 10 or at least 15.

The bond pattern may be imparted to the nonwoven web by heat, pressure or a combination of heat and pressure as well as by using ultrasonic bonding and by combinations of heat, pressure and/or ultrasonic bonding. A suitable technique to provide the bond pattern is by calender-bonding. Calender bonding may be accomplished by passing the nonwoven material through the nip between a pair of rotating calender rollers, thereby compressing and consolidating the fibers to form the nonwoven web. One or both of the calender rollers may be heated, so as to promote plastic deformation, intermeshing and/or thermal bonding/fusion between superimposed and closely neighboring fibers compressed at the nip. The calender rollers may form operable components of a bonding mechanism in which they are urged together by a controllable amount of force, so as to exert the desired compressing force/pressure at the nip in some processes heating may be deemed unnecessary, since compression alone may generate sufficient energy within the fibers to effect bonding, resulting from rapid deformation and frictional heat generated in the fibers as they are urged against each other where they are superimposed and closely neighboring, resulting in plastic deformation and intermeshing, and possibly thermal bonding/fusion.

In some processes an ultrasonic energy source may be included in the bonding mechanism so as to transmit ultrasonic vibration to the fibers, again, to generate heat energy within them and facilitate or enhance bonding.

One or both of the calender rollers may have their circumferential surfaces machined, etched, engraved or otherwise formed to have thereon a pattern of protrusions and recessed areas, so that bonding pressure exerted on the nonwoven material at the nip is concentrated at the outward surfaces of these protrusions, and reduced or substantially eliminated at the recessed areas. As a result, an impressed pattern of bonds between fibers forming the nonwoven web, generally corresponding to the pattern of protrusions on the calender roller, is formed in the nonwoven web. One calender roller may have a smooth, unpatterned surface, and the other may be formed with a pattern as described; this combination will impart a pattern on the web generally reflecting the pattern on the formed calender roller. In some examples both calender rollers may be formed with patterns, and in particular examples, differing patterns that work in combination to impress a combination pattern on the web such as described in, for example, U.S. Pat. No. 5,370,764.

A repeating pattern of protrusions and recessed areas may be imparted to one calender roller. For example, the protrusions on the calender roll may be rhombus-, diamond-, or otherwise shaped raised surfaces of protrusions, while the areas between them represent recessed areas. Without intending to be bound by theory, it is believed that the visual impact of the bond impressions impressed on the nonwoven web, as well as the tensile strength, resulting from the protrusion surfaces, may be affected by the area of the protrusion surfaces. Accordingly, it is believed desirable that the area of the individual protrusion surfaces be from at least 0.3 mm², or at least 0.4 mm² or at least 0.5 mm² or at least 0.5 mm²; they may also be no more than 10 mm² or no more than 5 mm². If the individual protrusion areas are not ail similar in size, the size of ail individual protrusion areas may be in the range of from 0.3 mm² to 10 mm² or from 0.4 mm² to 8 mm² or from 0.5 mm² to 8 mm². Protrusion surfaces may have diamond shapes as shown, or may have any other suitable shape, although it is believed that a diamond, rectangle, square or oval shape may have the desirable effect of simulating the appearance of stitching, as in a quilt.

Protrusion surfaces on the calender roll may be arranged such that the recessed areas are island-like areas which are surrounded by a continuous area of protrusions (i.e. raised areas). The resulting, nonwoven web will then have a continuous bonded, areas which delimits a plurality of individual unbonded areas. The recessed areas on the calender roll may be in the form of geometric shapes. The geometric shapes may be diamonds or squares, or may have other shapes, including but not limited to triangles, diamonds, parallelograms, stars, other polygons, circles, hearts, moons, etc.

Test Methods

Measurement of Delta E*

Bonded Versus Unbonded Color Difference Analysis

The bonded pattern color difference measurement is based on the CIE L*a*b* color system (CIELAB). A flat bed scanner capable of scanning a minimum of 24 bit color at 1200 dpi and has manual control of color management (a suitable scanner is an Epson Perfection V750 Pro from Epson America Inc., Long Beach Calif.) is used to acquire images. The scanner is calibrated against a color reflection target compliant to ANSI method IT8.7/2-1993 using color management software (a suitable package is MonacoEZ-Color available from X-Rite Grand Rapids, Mich.) to construct a scanner profile. The resulting calibrated scanner profile is opened within an imaging program that supports sampling in CIE L*a*b* (a suitable program is Photoshop S4 available from Adobe Systems Inc., San Jose, Calif.) to measure bonded and unbonded areas.

Turn on the scanner for 30 minutes prior to calibration. Place the IT8 target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight. Crop the image to the edge of the target, excluding all white space around the target, and acquire the final image. The MonacoEZColor software uses this image to compare with included reference files to create and export a calibrated color profile compatible with Photoshop. After the profile is created the scan resolution (dpi) can be changed, but all other settings must be kept constant while imaging samples.

Remove a piece of the nonwoven web. For convenience of handing, the sample size may be a 75 mm by 75 mm piece, however, as will be appreciated by the person skilled in the art, smaller samples sizes can be used. If the nonwoven web needs to be removed from a product, such as an absorbent article, it may be necessary to use a cryogenic freeze spray (e.g. CytoFreeze, Control Company, Tex.) to remove the specimen from the product. Precondition samples at about 23° C.±2 C.° and about 50%±2% relative humidity for 2 hours prior to testing.

Open the scanner lid and place the specimen onto the scanner glass. If the nonwoven web has additional layers and the layer comprising or consisting of the multicomponent fibers described in claim 1 form (only) one of the outer surfaces of the nonwoven web, the surface comprising or consisting of these multicomponent fibers has to face the glass. Cover the specimen with the white background (in this test method white is defined as having L*>94, −2<a*<2, and −2<b*<2) and close the lid. Acquire and import a scan of the specimen into Photoshop at 600 dpi and 24 bit color. Assign the calibrated scanner profile to the image and change the mode to Lab Color ("Lab Color" in Photoshop corresponds to the CIE L*a*b* standard). Select the "eyedropper" color selection tool. Set the sampling size of the tool to include as many pixels as possible within a bonded area without including pixels from adjacent unbonded areas. Using the eyedropper tool measure and record L*a*b* values in 10 different bonded areas in the nonwoven image. Average the 10 individual L*a*b* values and record as $L_1$, $a_1$ and $b_1$ respectively. Repeat the measure in like fashion for 10 different unbonded areas in the nonwoven image, and record the averaged values as $L_2$, $a_2$ and $b_2$. Calculate and report the color difference (delta E*) between the bonded and unbonded areas using the following equation:

$$\text{delta } E^* = \sqrt{(L_2^*-L_1^*)^2+(a_2^*-a_1^*)^2+(b_2^*-b_1^*)^2}$$

and report to the nearest 0.01 units. A total of three substantially identical nonwoven webs are measured for each sample set. Average the three delta E** values and report to the nearest 0.1 unit.

Other color analyses that may be useful are made using the calculations of delta Chroma (delta C*) and delta Hue (delta H*).

$$\text{Delta } C^* = \text{square-root}(a^*_1{}^2+b^*_1{}^2)-\text{square-root}(a^*_2{}^2+b_2{}^2)^2$$

$$\text{Delta } H^* = \text{square-root}[(a^*_2-a^*_1)^2+(b^*_2-b_1)^2-(\text{Delta}C^*)^2]$$

Image Analysis of Bond Impressions

Area and distance measurements are performed on images generated using a flat bed scanner capable of scanning at a resolution of at least 4800 dpi in reflectance mode (a suitable scanner is the Epson Perfection V750 Pro. Epson, USA). Analyses are performed using ImageJ software (Vs. 1.43u, National Institutes of Health, USA) and calibrated against a ruler certified by NIST.

Remove a piece of the nonwoven web. For convenience of handing, the sample size may be a 75 mm by 75 mm piece, however, as will be appreciated by the person skilled in the art, smaller samples sizes can be used. If nonwoven web needs to be removed from a product, such as an absorbent article, it may be necessary to use a cryogenic freeze spray (e.g. CytoFreeze, Control Company, Tex.) to remove the specimen from the product. Precondition samples at about 23° C.±2 C.° and about 50%±2% relative humidity for 2 hours prior to testing.

Place the specimen on the flat bed scanner, with the ruler directly adjacent If the nonwoven web has additional layers and the layer comprising or consisting of the multicomponent fibers described in claim 1 form (only) one of the outer surfaces of the nonwoven web, the surface comprising or consisting of these multicomponent fibers has to face the glass. Placement is such that one of the side edges of the nonwoven web sample is parallel to the ruler. A black backing is placed over the specimen and the lid to the scanner is closed. Acquire an image composed of the nonwoven web and ruler at 4800 dpi in reflectance mode in 8 bit grayscale and save the file. Open the image file in ImageJ and perform a linear calibration using the imaged ruler.

Average Individual Bond Area

Enlarge a region of interest such that edges of the bonded area can be clearly determined. With the area tool, manually trace the perimeter of a bonded, area. Calculate and record the area to the nearest 0.001 mm$^2$. Repeat for a total often non-adjacent bonded areas randomly selected across the total specimen. A total of three substantially identical nonwoven web samples are measured for each sample set. Calculate the average and standard deviation of all 30 bond area.

If the bond pattern is such that the individual bonded, areas are very different in size, the largest and the smallest bonded areas can each be determined as set out in the previous paragraph to determine the size range of the individual bonded areas.

Bond Area Percentage

Identify a single repeat pattern of bonded areas and unbonded areas and enlarge the image such that the repeat pattern fills the field of view. In ImageJ draw a box that encompasses the repeat pattern. If the bond pattern does not comprise a repeat pattern of bonded, areas, a number of different samples is taken and measured such that the bond area percentage can be determined as an average value from these samples to a satisfying extend. The numbers of samples necessary may depend on the how unhomogeneous the bond pattern is (the number of samples may be from 10 to 100 or even more). Calculate area of the box and record, to the nearest 0.01 mm$^2$. Next, with the area tool, trace the individual bonded area or portions thereof entirely within the box and calculate the areas of ail bonded areas or portions thereof that are within the box. Record to the nearest 0.01 mm$^2$. Calculate as follows:

Percent Bond Area=(Sum of areas of bond impressions within box)/(area of box)×100%

Repeat for a total of five non-adjacent regions of interest, randomly selected, across the total specimen. Record as Percent Bond Area to the nearest 0.01%. Calculate the average and standard deviation of ail of the percent bond area measurements and report to the nearest 0.001 units.

If the bond pattern consists of continuous bonded areas with individual unbonded areas dispersed therein, basically the same test method can be used, however, rather than tracing the individual bonded, areas, the unbonded areas are traced and the calculation is adjusted accordingly.

Opacity Measurement Method

The opacity of a material is the degree to which light is blocked by that material. A higher opacity value indicates a higher degree of light block by the material. Opacity may be measured using a 0.deg. illumination/45.deg. detection, circumferential optical geometry, spectrophotometer with a computer interface such as the HunterLab LabScan XE running Universal Software (available from Hunter Associates Laboratory Inc., Reston, Va.). Instrument calibration and measurements are made using the standard white and black calibration plates provided by the vendor. All testing is performed in a room maintained at about 23° C.±2° C. and about 50%±2% relative humidity. Configure the spectrophotometer for the XYZ color scale, D65 illuminant, 10.deg. standard-observer, with UV filter set to nominal. Standardize the instrument according to the manufacturer's procedures using the 1.20 inch port size and 1.00 inch area view. After calibration, set the software to the Y opacity procedure.

To obtain the specimen, a film having a thickness of 10 μm is of the material which is used for the first component or which is used for the component for which opacity shall be determined of the web of claim 1 has to be manufactured. Cut a piece 50.8 mm by 50.8 mm centered at each site. Precondition samples at about 23° C.±2° C. and about 50%±2% relative humidity for 2 hours prior to testing.

Place the specimen over the measurement port. The specimen should completely cover the port with the first outer surface directed toward the port. Cover the specimen with the white standard plate. Take a reading, then remove the white tile and replace it with black standard tile without moving the specimen. Obtain a second reading, and calculate the opacity as follows:

Opacity=$Y$ value[(black backing)/$Y$ value[(white backing)×100

A total of five substantially identical samples are analyzed and their opacity results recorded. Calculate and report the average opacity and standard deviation for the web measurements to the nearest 0.01%.

Colorfastness Measurement

Colorfastness of the nonwoven web is measured following test method AATCC (American Association of Textile Chemists and Colorists) 116-2005 titled "Colorfastness to Crocking: Rotary Vertical Crockmeter Method". With regard to item 1.2 of the test method, colorfastness is measured taking a dry sample. The size of the test specimen may be smaller than 1 inch$^2$, which is indicated in item 7 of the test method. E.g. the sample may be as small as 25 mm long and 10 mm wide.

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web comprising multicomponent fibers, wherein the multicomponent fibers have at least a first component comprising polyethylene and at least about 0.5 percent by weight $TiO_2$ and a second component comprising polypropylene and a non-white pigment, the second component forming less than about 20% of the outer surface of the multicomponent fibers,
   wherein the first and the second component differ from each other in color,
   the nonwoven web being pattern bonded, wherein the bonded areas have a first color and the unbonded areas have a second color which is different from the first color, the difference between the first color of the bonded areas and the second color of the unbonded areas substantially being induced by the difference in color of the components of the multicomponent fibers,
   and wherein a delta E* between the bonded areas and the unbonded areas is at least about 0.5, as determined by the Measurement of delta E* method described herein.

2. The nonwoven web according to claim 1, wherein the multicomponent fibers are fused together in the bonded areas.

3. The nonwoven web according to claim 1, wherein the first component forms at least about 50% of the outer surface of the multicomponent fibers.

4. The nonwoven web according to claim 1, wherein the first component has an opacity greater than about 30%, as measured by the Opacity Measurement Method described herein.

5. The nonwoven web according to claim 1, wherein the first component constitutes about 40% or more by weight of the multicomponent fibers.

6. The nonwoven web according to claim 1, wherein the second component constitutes about 40% or more by weight of the multicomponent fibers.

7. The nonwoven web according to claim 1, wherein the multicomponent fibers are core-sheath bicomponent fibers and wherein the first component forms the sheath and the second component forms the core of the bicomponent fibers.

8. The nonwoven web according to claim 1, wherein the multicomponent fibers comprise one or more additional component(s) and wherein the one or more additional component(s) form at least about 30% of the outer surface of the fibers and comprise $TiO_2$.

9. The nonwoven web according to claim 1, wherein the multicomponent fibers comprise one or more additional component(s) and wherein the one or more additional component(s) form less than about 20% of the outer surface of the fibers and comprise a non-white pigment.

10. A disposable absorbent garment comprising the nonwoven web according to claim 1.

11. The nonwoven web according to claim 10, wherein the disposable absorbent article is selected from the group consisting of a diaper, a pant, a sanitary napkin and an absorbent insert for a diaper or pant, wherein the nonwoven web forms the topsheet, the backsheet, the back ears, the front ears, the landing zone, the elasticized leg cuffs and/or the barrier leg cuffs of the disposable absorbent article.

12. A disposable cleaning article comprising the nonwoven web according to claim 1.

* * * * *